United States Patent [19]

Drabick et al.

[11] 4,307,084

[45] Dec. 22, 1981

[54] PORPHINE-CARBOHYDRATE-FATTY ACID COMPLEXES AS SYNTHETIC RESPIRATORY PIGMENTS

[75] Inventors: Joseph J. Drabick, Philadelphia; Saul I. Shupack, Wayne, both of Pa.

[73] Assignee: Villanova University, Villanova, Pa.

[21] Appl. No.: 211,199

[22] Filed: Nov. 28, 1980

Related U.S. Application Data

[63] Continuation-in-part of Ser. No. 142,859, Apr. 21, 1980, abandoned.

[51] Int. Cl.³ .................... A61K 31/40; C07D 487/22; C09B 47/00
[52] U.S. Cl. ..................................... 424/180; 536/51; 536/112; 536/113; 260/314
[58] Field of Search ................ 424/180; 536/112, 113; 260/314

[56] References Cited

PUBLICATIONS

Datta-Gupta et al., J. Heterocyclic Chem. vol. 3, pp. 495–502 (1966).
Aronson et al., Chem. Abstracts, vol. 80,. abst. 12155u (1974).
Messmer et al., Chem. Abstracts, vol. 82, abst. 68435 (1975).
Tsuchida et al., Biochim. Biophys. Acta, vol. 427, pp. 520–529 (1976).
Jones et al., Chem. Reviews, vol. 79, pp. 139 to 175 (1979) (note especially pp. 140–147).

*Primary Examiner*—John D. Randolph
*Attorney, Agent, or Firm*—James Albert Drobile

[57] ABSTRACT

An aqueous, biologically-compatible, reversible, oxygen-carrying system comprising a novel metallated porphine-carbohydrate-fatty acid complex, particularly a novel tetra-(p-carboxyphenyl)porphine-iron(II)-dextran-octanoate complex, useful as a synthetic respiratory pigment, and a method for preparing same. The complexes may be dissolved in a suitable electrolyte and used as a substitute for red blood cells.

17 Claims, No Drawings

PORPHINE-CARBOHYDRATE-FATTY ACID COMPLEXES AS SYNTHETIC RESPIRATORY PIGMENTS

CROSS-REFERENCE TO RELATED APPLICATION

This application is a continuation-in-part of copending application Ser. No. 142,859, filed Apr. 21, 1980, now abandoned.

FIELD OF THE INVENTION

This invention relates to a novel synthetic oxygen carrier system capable of reversibly binding oxygen and useful for storing and transporting oxygen in biological systems and as a substitute for red blood cells, and to a method for preparing the same.

To be classified as an oxygen carrier, a system or compound must reversibly bind oxygen, i.e. the complex formed with oxygen must be able to dissociate to give the original complex (ML) and oxygen:

$$ML + O_2 \rightleftharpoons [ML-O_2]$$

The process of dissociation can be observed by lowering the ambient partial pressure of $O_2$, by heating the oxygen-containing complex ($[ML-O_2]$), or by the addition of a ligand capable of replacing the bound $O_2$.

DESCRIPTION OF THE PRIOR ART

Considerable research has been conducted relating to complexes capable of reversibly binding $O_2$ and having binding characteristics comparable to the natural oxygen carriers of vertebrates, namely, hemoglobin and myoglobin. These natural protein-containing carriers combine reversibly with oxygen in blood and tissues by virtue of a heme (iron(II)-porphyrin) prosthetic group. One $O_2$ molecule is bound for each ferrous ion which is chelated to the four core nitrogen atoms of the porphyrin complex. In these and other heme proteins of vertebrates the porphyrin is embedded in a polypeptide chain having a molecular weight of from about 16,000 to about 60,000 daltons.

Several known synthetic oxygen carriers, like the natural oxygen carriers, contain porphyrins or porphyrin related compounds. These porphyrins all can be viewed as derived from the parent compound, porphine. Two of the most commonly studied synthetic porphyrins are meso-tetraphenylporphyrin and octaethyl-porphyrin.

Research on synthetic oxygen carriers has dealt largely, but not exlusively, with complexes containing the elements iron, cobalt or manganese. Further work involving these metals combined with the porphyrin-related compounds mentioned above, including porphine derivatives, has also been performed. It has been shown that, under the proper conditions, iron(II)-porphyrin complexes react reversibly with oxygen and are, therefore, potentially useful in synthetic oxygen carrier systems.

A major difficulty concerning the use of these iron-(II)-Porphyrin complexes is the tendency for them to undergo rapid irreversible oxidation without detectible formation of the iron-oxygen complex, presumably due to the formation of a dimer of the iron(II)-porphyrin complex.

Two approaches have been taken in the design of a model system for reversibility studies. These approaches involve (1) synthesis of complexes containing steric hindrances to dimer formation and (2) complexes attached to a rigid surface to prevent contact between iron atoms. Studies on these synthetic complexes were conducted in non-polar systems and therefore are of virtually no practical utility in the aqueous environment of living organisms.

Several reports of reversible binding to synthetic iron(II)-porphyrin oxygen carriers have been published, including the work of Tsuchida, et al., Biochim. Biophys. Acta, 427: 520(1976) demonstrating a poly-L-lysine-protoporphyrin-iron(II) polymer. See also Jones, et al., Chem. Rev., 79: 139(1979).

The requirements for optimal use of any synthetic respiratory system are rigorous indeed. There must be minimal adverse immunological response over the period of use and the system component or components must be large enough to be retained by the kidneys and of sufficient molecular weight so as to minimize osmotic flux. It is additionally desirable that the system component(s) break down at a slow enough rate so as to allow red blood cell (RBC) replenishment, and that the disintegration products be readily metabolized. Further, an ideal system would be of sufficient viscosity to prevent vascular shock.

SUMMARY OF THE INVENTION

Accordingly, it is an object of the present invention to provide novel compounds or complexes and compositions of matter useful as synthetic respiratory materials and fulfilling the requirements set forth above.

It is another object of the present invention to provide aqueous, biologically-compatible, reversible, oxygen-carrying systems comprising a novel complex or compound of this invention.

It is another object of the invention to provide novel metallated porphine-carbohydrate-fatty acid complexes or compounds, and compositions of matter containing same, useful for transporting oxygen and as a substitute for red blood cells.

It is a further and specific object of this invention to provide the novel complexes or compounds, tetra-(p-carboxyphenyl)porphine-iron(II)-dextran-octanoate complexes or compounds, and compositions containing same.

It is yet another object of the present invention to provide compounds and compositions useful as anti-vasodilators.

It is still another object of the invention to provide methods for preparing the novel complexes or compounds of the invention, including the novel tetra-(p-carboxyphenyl) porphine-iron(II)-dextran-octanoate complexes.

Still other advantages, objects and characteristics of the present invention may be realized from the accompanying detailed description and examples.

The novel porphine-carbohydrate-fatty acid complexes or compounds of the invention (herein, sometimes "PCF"), for example, tetra-(p-carboxyphenyl)-porphine-iron(II)-dextranoctanoate complexes, are found to bind molecular oxygen reversibly at room temperature. Since the complex is water soluble it may be dissolved in plasma, physiological saline or any physiologically acceptable electrolyte solution, and may be used as a red blood cell substitute. As used herein, the term "physiologically acceptable electrolyte solution" includes those solutions of an electrolyte or electrolytes adapted for injection. Illustrative are lactated potassic saline injection, Ringer's injection, lactated Ringer's injection, Ringer's solution, lactated Ringer's solution, sodium acetate, sodium chloride and sodium lactate injection. These and other preparations are described in Remington's Pharmaceutical Science, 13th Edition, pages 914–922 (1965) under the heading "electrolytes." Other plasma expanders are described in Goodman and Gillman, The Pharmacological Basis of Therapeutics, 3rd Edition, pages 754–794 (1965). The disclosures of both of these references are incorporated herein by reference.

Since dextran has been used for years as a blood expander in man with minimal side effects for short term use, there should be no significant immunological reaction surrounding use of the novel complexes or compounds in human blood. The complexes or compounds and the compositions of the invention further satisfy the requirements for a useful synthetic respiratory material, and overcome the disadvantages of the prior art systems and materials in that they are retained by the kidneys, will not significantly interfere with osmotic flux, and will naturally disintegrate at an acceptable rate into readily metabolizable products. Additionally, the complexes or compounds function as antivasodilators.

According to the method and theory of the invention, covalent ester linkages are formed between a metallated water-soluble porphine and a high molecular weight dextran. To the dextran moiety of the metalloporphine-dextran product are linked short-chain fatty acids having from about six (6) to about ten (10) carbon atoms, as described more fully below.

DETAILED DESCRIPTION, INCLUDING PREFERRED EMBODIMENT

Known procedures are used for the synthesis of tetra-($\alpha,\beta,\gamma,\delta$-p-carboxyphenyl)porphine-iron(III), in particular, the method described by F. R. Longo, M. G. Finarelli and J. B. King in Journal of Heterocyclic Chemistry, Volume 6, page 927 (1969).

It should be noted that other water-soluble porphine compounds also can be utilized, provided they have functional groups that allow chemical attachment to a dextran. Examples of other water-soluble porphine compounds which are suitable for use in accordance with the present invention are: tetraphenylporphinesulfonate and tetra(N-methyltetrapyridyl) porphine (see R. F. Pasternack, P. R. Huber, P. Boyd, G. Engasser, L. Francesconi, E. Gibbs, P. Fasella, G. Cerio Venturo, and L. deC. Hinds, Journal of the American Chemical Society, Volume 94, pages 4511–4517 (1972).

In accordance with the novel method of the invention, the metalloporphine-dextran complex or compound is prepared as hereinafter described. An aqueous solution of from about 0.02 to about 3 weight percent of a dextran having a molecular weight in the range of from about 50,000 to about 275,000 is prepared. Another solution is prepared, consisting of from about 0.01 to about 2 weight percent (based on the weight of the aqueous dextran solution) of a ferric iron complex of a water-soluble porphine compound selected from the group consisting of (1) tetra-($\alpha,\beta,\gamma,\delta$-p-carboxyphenyl)porphine; (2) tetraphenylporphinesulfonate; and (3) tetra(N-methyltetrapyridyl)porphine, in a minimum amount of an aqueous solution of sodium hydroxide (pH about 10). Still another solution is prepared, consisting of from about 0.005 to about 1.0 weight percent (based on the weight of the aforementioned aqueous dextran solution) of N,N'-dicyclohexylcarbodiimide in a minimum amount of acetone.

The three solutions prepared as above described are combined and are stirred for an extended period of time, say for approximately one hour, and at an elevated temperature, say at about 50° C.

The alkanoate of the metalloporphine-dextran complex is prepared as follows. To the combination of the dextran solution, the solution of the porphine-iron(III) complex, and the N,N'-dicyclohexylcarbodiimide solution, prepared and combined as above described, is added (1) from about 0.005 to about 1.0 weight percent (based on the weight of the aqueous dextran solution), of an alkanoic or fatty acid selected from the group consisting of alkanoaic acids having from six (6) to ten (10) carbon atoms, and (2) another solution consisting of from about 0.005 to about 1.0 weight percent (based on the weight of the aqueous dextran solution), of N,N'-dicyclohexylcarbodiimide in a minimum amount of acetone, and the resulting solution or mixture is stirred for an extended period of time, say for approximately one hour and, at an elevated temperature, say at about 50° C. The composite solution then is evaporated to dryness by continued heating at an elevated temperature of about 50° C., while circulating air over its surface. The resulting solid is washed with ethanol, N,N-dimethylformamide and/or acetone, and is again redissolved in deionized water and taken to dryness one or more times.

It should be noted that N,N'-dicyclohexylcarbodiimide is a known standard peptide coupling agent, and that a solution of another such coupling agent in an appropriate solvent can be utilized in accordance with the present invention in place of the solutions of N,N'-dicyclohexylcarbodiimide in acetone referred to above. Examples of other known standard peptide coupling agents are: N,N-carbonyldiimidazole; 1-cyclohexyl-3-(2-morphonlinoethyl)-carbodiimide metho-p-toluenesulfonate; 1-ethyl-3-(3-dimethylaminopropyl)-carbodiimide hydrochloride; N-hydroxysuccinimide; N-trifluoroacetylimidazole; N,N'-carbonyldiimidazole; isobutylchloroformate; and di- and tetra-esters of pyrophosphoric acid. See also Pettit, Synthetic Peptides, volume 2, chapter 2 (Van Nostrand Reinhold Company-1971). Suitable solvents for these other standard peptide coupling agents are also well known, and include such solvents as acetic acid, collidine, dimethylformamide, dimethyl sulfoxide, ethyl acetate, ethylene dichloride, N-ethyl morpholine, methanol, methylene chloride, N-propanol, pyridine, toluene and triethylamine. In general, any polar solvent which does not react with the coupling agent can be used. Solutions containing from about 0.001 to about 5.0 weight percent, based on the weight of the aqueous dextran solution, of the standard peptide coupling agent in a minimum amount of a suitable solvent can be utilized in place of the specified solutions of N,N'-dicyclohexylcarbodiimide in acetone. More particularly, it is desirable to provide in such a solution from about 0.001 to about 1.0 moles of the coupling agent per hydroxyl group in the dextran of the aqueous dextran solution.

SPECIFIC EXAMPLE

Free Base Porphine

A propanoic acid solution, 0.24 molar in both 4-carboxybenzaldehyde and pyrrole, is refluxed for two hours. When the solution is cooled, the tetra-($\alpha,\beta,\gamma,\delta$-p- carboxyphenyl)porphine precipitates as purple crystals. Further purification is effected by recrystallization from methanolchloroform solutions.

Porphine-Iron(III) Complex

To a refluxing dimethylformamide solution of the above-prepared porphine compound (about $10^{-4}$ molar) is added, in 10 percent mole excess, commercially-obtained anhydrous ferric chloride. Reaction is continued until the red fluorescent character of the free base porphine ceases—approximately 30 minutes. Removal of the solvent leaves essentially a pure product, and excess metal chloride which is removed by washing with water. Further purification is effected by column chromatography using neutral alumina, and benzene or chloroform elutants.

Metallated Porphine-Dextran

To 250 ml of deionized water is added 0.5 grams ($6.67 \times 10^{-6}$ moles) of dextran (75,000 M.W.), plus enough sodium hydroxide (NaOH) to insure the formation of a sufficient number of sodium alcoholates but not enough to cause significant hydrolysis of the dextran (pH=10, 0.4 g, $1 \times 10^{-2}$ moles). Alternatively, any dextran ranging in molecular weight from about 50,000 to 275,000 may be used. A 0.22 g sample of the above-prepared carboxylated-metallo-porphine complex ($2.79 \times 10^{-4}$ moles) is dissolved in a minimum amount of water/NaOH solution (pH=10), and an excess N,N'-dicyclohexylcarbodiimide (0.1 g, $5 \times 10^{-3}$ moles, equivalent to $1 \times 10^{-2}$ esterification units) is dissolved in a minimum amount of acetone.

Both the carboxylated metallo-porphine solution and the carbodiimide solution then are added simultaneously to the dextran solution. The resulting solution is stirred for approximately 1 hour at about 50° C.

Porphine-Dextran-Fatty Acid

Next, 0.18 grams of octanoic acid ($1.25 \times 10^{-3}$ moles) and a carbodiimide solution (similar to the previously mentioned carbodiimide solution) are added to the aboveprepared carboxylated metallo-porphine-dextran carbodiimide solution and again stirred for about one hour at about 50° C. The composite solution is then evaporated to dryness by continued heating (50° C.) while air is circulated over the surface of the solution.

The resulting solid (greenish) is washed with ethanol, N,N-dimethylformamide and acetone, and is redissolved in deionized water and taken to dryness once more. The solid is analyzed and is reported by Galbraith Laboratories, of Knoxville, Tennessee as follows: carbon 42.72%; hydrogen, 6.94%; iron, 0.05%. This analysis can be fitted to a molecule or complex consisting of about 55–60 octanoate groups, one metallated porphine and one dextran group.

Similar syntheses but employing other alkanoic or fatty acids having from about six (6) to about ten (10) carbon atoms also provide compounds or complexes which are suitable for use in accordance with the present invention.

Testing

The compound of Example 1 (hereafter "PCF") is tested by using the $^PO_2$ meter and electrode system of Radiometer/Copenhagen. Sodium thiosulfate solutions (3 molar) are used to give the iron(II) state. Alternatively, the iron(III) complex or compound can be reduced by Zn° prior to being placed in distilled water. Comparisons are made with human blood and solutions containing everything but porphine. Solutions are allowed to equilibrate with oxygen in the air. The $^PO_2$ electrode measures dissolved $O_2$, because the PCF complex or compound removes it from solution. In order to test the "reversibility" of $O_2$ uptake, samples are placed under vacuum for 15 min. and then re-exposed to air for 5 min. The $^PO_2$ is then measured. All values are relative measurements and not absolute values. Furthermore, the $^PO_2$ values of equal volumes of solvent are used to correct for solution comparisons. Studies also are made with human blood.

Tests conducted as above described in 3-molar $Na_2S_2O_3$ indicated a $^PO_2$ binding of 90 mmHg for PCF and 110 mmHg for human blood. Tests conducted in water, in which the iron had previously been reduced over zinc, resulted in a $^PO_2$ binding of 60 mmHg for PCF and of 7 mmHg for human blood.

Reversibility studies indicated a $^PO_2$ value of 12 mmHg for PCF and 7 mmHg for human blood.

The invention claimed is:

1. A process for making a synthetic respiratory pigment, comprising:
   (a)
   (i) preparing an aqueous solution of from about 0.02 to about 3 weight percent of a dextran having a molecular weight in the range of from about 50,000 to about 275,000 and
   (ii) preparing a solution of from about 0.01 to about 2 weight percent, based on the solution of (a)(i), of a ferric iron complex of a water-soluble porphine compound selected from the group consisting of: tetra-($\alpha,\beta,\gamma,\delta$-p-carboxyphenyl) porphine; tetraphenylporphinesulfonate; and tetra(N-methyltetrapyridyl)porphine, in a minimum amount of an aqueous solution of sodium hydroxide;
   (b) preparing a solution of from about 0.001 to about 5.0 weight percent, based on the weight of the solution of (a)(i), of a standard peptide coupling agent in a minimum amount of a suitable solvent,
   (c) combining the solutions prepared in (a) and (b) and stirring for an extended period of time at an elevated temperature,
   (d) adding to the product of (c) from about 0.005 to about 1.0 weight percent, based on the weight of the solution of (a)(i), of an alkanoic acid selected from the group consisting of alkanoic acids having from six (6) to ten (10) carbon atoms, and another solution of from about 0.001 to about 5.0 weight percent, based on the weight of the solution of (a)(i), of a standard peptide coupling agent in a minimum amount of a suitable solvent, and stirring the resultant mixture for an extended period of time at an elevated temperature, and
   (e) evaporating the product of (d) to dryness.

2. The process of claim 1, wherein the solution of a standard peptide coupling agent is a solution of from about 0.001 to about 5.0 weight percent, based on the weight of the aqueous dextran solution, of N,N'-dicyclohexylcarbodiimide in a minimum amount of acetone.

3. The process of claim 1, wherein the ferric iron complex of the water-soluble porphine compound is tetra-($\alpha,\beta,\gamma,\delta$-p-carboxyphenyl)porphine-iron III.

4. The process of claim 1, wherein the alkanoic acid is octanoic acid.

5. The process of claim 1, wherein the ferric iron complex of the water-soluble porphine compound is tetra-($\alpha,\beta,\gamma,\delta$-p-carboxyphenyl) porphine-iron III and the alkanoic acid is octanoic acid.

6. The process of claim 1, further comprising the step of:

(f) reducing the product of step (e).

7. A product of the process of claim 1.

8. A product of the process of claim 5.

9. A product of the process of claim 1, wherein the molecular ratio of metallated porphine:dextran:alkanoate is about 1:1:40-80.

10. A product according to claim 8, wherein the ratio is about 1:1:60.

11. A composition comprising from about 2 to about 60 weight percent, based on total weight, of a product of claim 6 dissolved in a medium selected from the group consisting of plasma and a physiologically acceptable electrolyte solution.

12. A composition of claim 11, where the electrolyte solution is saline.

13. A composition of claim 11, where the electrolyte solution is lactated Ringer's solution.

14. A composition comprising from about 2 to about 60 weight percent, based on total weight, of a tetra-($\alpha,\beta,\gamma,\delta$-p-carboxyphenyl)porphine-iron (II)-dextran-alkanoate complex wherein the dextran moiety has a molecular weight in the range of from about 50,000 to about 275,000 and the alkanoate moiety is derived from an alkanoic acid having from about 6 to about 10 carbon atoms, in a medium selected from the group consisting of plasma and a physiologically acceptable electrolyte solution.

15. A composition according to claim 14 wherein the dextran moiety has a molecular weight of about 75,000 and the alkanoate moiety is derived from octanoic acid.

16. A composition comprising from about 2 to about 60 weight percent, based on total weight, of a tetra-(phenylporphinesulfonate-iron-(II)-dextran-alkanoate complex wherein the dextran moiety has a molecular weight in the range of from about 50,000 to about 275,000 and the alkanoate moiety is derived from an alkanoic acid having from about 6 to about 10 carbon atoms, in a medium selected from the group consisting of plasma and a physiologically acceptable electrolyte solution.

17. A composition comprising from about 2 to about 60 weight percent, based on total weight, of a tetra-(N-methyltetrapyridyl)porphine-iron(II)-dextran-alkanoate complex wherein the dextran moiety has a molecular weight in the range of from about 50,000 to about 275,000 and the alkanoate moiety is derived from an alkanoic acid having from about 6 to about 10 carbon atoms, in a medium selected from the group consisting of plasma and a physiologically acceptable electrolyte solution.

* * * * *